United States Patent
Koshti et al.

(10) Patent No.: US 10,758,467 B2
(45) Date of Patent: Sep. 1, 2020

(54) HIGHLY SUBSTANTIVE WATER-SOLUBLE UV ABSORBERS AND PROCESS FOR PREPARATION THEREOF

(71) Applicant: GALAXY SURFACTANTS LTD., Maharashtra (IN)

(72) Inventors: Nirmal Koshti, Piscataway, NJ (US); Bhagyesh Jagannath Sawant, Maharashtra (IN)

(73) Assignee: GALAXY SURFACTANTS LTD. (IN)

( * ) Notice: Subject to any disclaimer, the term of this patent is extended or adjusted under 35 U.S.C. 154(b) by 0 days.

(21) Appl. No.: 16/269,077

(22) Filed: Feb. 6, 2019

(65) Prior Publication Data
US 2019/0343744 A1    Nov. 14, 2019

(30) Foreign Application Priority Data
May 11, 2018    (IN) .............................. 201821017746

(51) Int. Cl.
| | | |
|---|---|---|
| A61K 8/41 | (2006.01) | |
| A61Q 17/04 | (2006.01) | |
| A61Q 5/06 | (2006.01) | |
| C07C 237/10 | (2006.01) | |
| A61Q 5/12 | (2006.01) | |
| C07C 231/12 | (2006.01) | |
| A61Q 5/02 | (2006.01) | |

(52) U.S. Cl.
CPC .............. *A61K 8/416* (2013.01); *A61Q 5/02* (2013.01); *A61Q 5/06* (2013.01); *A61Q 5/12* (2013.01); *A61Q 17/04* (2013.01); *C07C 231/12* (2013.01); *C07C 237/10* (2013.01)

(58) Field of Classification Search
CPC ........ A01N 1/00; A61K 8/416; A61Q 17/005; A61Q 17/04; A61Q 5/02; A61Q 5/06; A61Q 5/12; C07C 231/12; C07C 233/40; C07C 235/34; C07C 237/10
USPC ........................................................... 424/59
See application file for complete search history.

*Primary Examiner* — Johann R Richter
*Assistant Examiner* — Courtney A Brown
(74) *Attorney, Agent, or Firm* — Fox Rothschild LLP

(57) ABSTRACT

Disclosed herein are water-soluble UV absorbing compounds of Formula I with two quaternary ammonium centers, wherein;

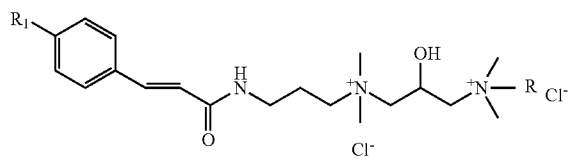

Formula I

R is selected from saturated or unsaturated alkyl groups with $C_{12}$ to $C_{22}$ carbon atoms and $R_1$ is selected from H or methoxy group. The invention further discloses the synthesis of highly substantive water-soluble UV absorbers containing two quaternary ammonium centers, cinnamidopropyl (2-hydroxypropyl alkyl dimethyl ammonium chloride) dimonium chlorides of Formula I and the compositions containing the same in personal care products.

6 Claims, 1 Drawing Sheet

HIGHLY SUBSTANTIVE WATER-SOLUBLE UV ABSORBERS AND PROCESS FOR PREPARATION THEREOF

FIELD OF INVENTION

The present invention relates to highly substantive quaternized water-soluble UV-absorbing compounds of Formula I wherein;

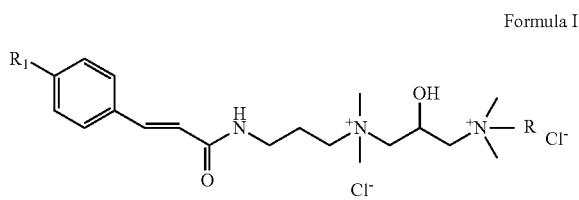

Formula I

R is selected from saturated or unsaturated alkyl groups with $C_{12}$ to $C_{22}$ carbon atoms and $R^1$ is selected from either H or methoxy group. The invention further relates to process for preparation of the UV-absorbing compounds of Formula I and personal care compositions containing the compounds of Formula I.

Background and Prior Art

Sunscreens formulations in the form of creams, lotions and sprays are not only used for recreational activity involving significant exposure to sunlight but also for daily protection of skin from the normal exposure to light as a part of long term anti-aging regime. These formulated sunscreen products use both organic (octocrylene, octyl methoxycinnamate) as well as inorganic ingredients (zinc oxide, titanium oxide etc.). Every ingredient has its merits and demerits, for example, inorganics are finely divided powders and they form a white film on the applied area. Some organic ingredients are solids that are neither soluble in oil nor in water (for example, Tinosorb M). In addition to the limitations arising out of physical nature of substance while formulating, there are limits set by the regional regulatory bodies on the allowed/permissible usage levels of these ingredients.

Synthetic sunscreens can be either oil-soluble or water-soluble and formulators use them judiciously depending upon the design (cream, lotion, spray) and the end-application (skin or hair, desired SPF/UV A protection factor).

Water-soluble UV-absorbers have their place in sunscreen formulations. In a cream type (emulsion) formulation water-soluble UV absorbers are accommodated in water phase of an o/w type emulsion wherein synergistic boosting of SPF is often seen with oil-soluble UV absorbers. Needless to say that water-soluble UV absorbers are the best in water based formulae like lotions, solutions, sprays and gels.

In the absence of a water-soluble yet significantly substantive UV absorber alternative, the formulators have been using non-substantive water-soluble UV absorbers (benzophenone-4 (B-4), phenyl benzimidazole sulphonic acid (PBSA), p-methoxy cinnamidopropyl dimethyl hydroxyl sultaine (Galaxy SunBeat) and cinnamidopropyl trimethyl ammonium chloride (Incroquat UV 283) along with other conditioners like cetrimonium chloride, guar hydroxypropyl trimonium chloride, or behenyl trimethyl ammonium chloride (Table I). These facts have been highlighted by Koshti et al. (U.S. Pat. No. 9,463,337).

TABLE I

| Product in Market | Manufacturer | UV absorber |
| --- | --- | --- |
| Dove Hair Therapy Reparatur-Pflege Color Schutz Shampoo | Unilever, Germany | B-4 |
| Dove Hair Therapy Damage Solutions Colour Radiance Shampoo | Unilever, Australia | B-4 |
| Nivea Color Care & Protect Colour Protection Shampoo | Beiersdorf, Austria | B-4 |
| Schlecker AS Haircare Colour Shine Conditioning Hair Mask | Schlecker, Spain | B-4 |
| Schwarzkopf Schauma Color Glanz Colour Protection Shampoo | Schwarzkopf and Henkel, Germany | B-4 |
| Schwarzkopf Schauma Color Glanz Colour Protection Conditioner | Schwarzkopf and Henkel, Germany | B-4 |
| L'Oréal Professionnel Série Expert Vitamino Color A-OX 10 in 1 Perfecting Multipurpose Spray | L'Oreal, USA | B-4 |
| Dove Hair Therapy Reparatur-Pflege Intensiv Reparatur Detangling Nourishing Spray | Unilever, Germany | B-4 |
| Pola Form Protection Mist | Pola, Japan | PBSA, OMC |
| Paul Mitchell Awapuhi Wild Ginger Style Texturizing Sea Spray | John Paul Mitchell Systems, USA | Crodasorb UV 283 (Cinnamidopropyltrimonium Chloride) Old Product Name: Incroquat UV-283 |
| Redken Color Extend Conditioner | Redken, UK | B-4 |
| Xtreme Wet Line Professional Attraction Power Gel for Men | Schwarzkopf & Henkel, Colombia | Galaxy SunBeat |
| Wet Line Xtreme Professional Styling Gel | Henkel, Mexico | Galaxy SunBeat |

The major drawback for water-soluble UV absorbers stems from the fact that they get washed away easily in rinse-off formulations. The commercially available water-soluble UV absorbers are Benzophenone-4 (CAS No 27503-81-7), Phenyl benzimidazole sulphonic acid (CAS No 4065-45-6) and methoxycinnamidopropyl hydroxyl sultaine CAS No 500731-87-3). The first two water-soluble molecules are sodium salts of sulphonic acids and the third one is a zwitterionic molecule with phenomenal water-solubility. All of them suffer from the disadvantage of not being substantive to negatively charged hair or skin surface.

This problem has been partially addressed by a water-soluble quaternized UV absorber which is substantive to negatively charged surface of skin and hair and is commercially available from Croda (Incroquat UV 283, Formula IV, cinnamidopropyl trimethyl ammonium chloride).

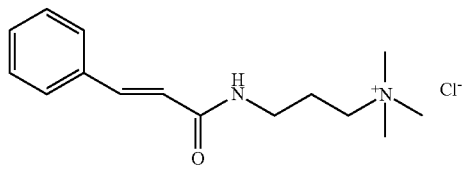

There are a few other quaternized UV absorbers commercially available, however, these are water-insoluble (Formula V and Formula VI). Being water-insoluble UV absorbers makes these molecules (U.S. Pat. No. 7,202,204 (2007), Quaternium 95, ChromAveil from Croda, Formula V and U.S. Pat. No. 9,463,337 (2016); GalHueShield from Galaxy Surfactants Ltd, Formula VI) completely unsuitable for water based formulations like transparent gels or solvent-free sunscreen sprays that can be used for both body and hair.

The other limitation is the lack of extended conjugation (no electron donating substituent on the benzene ring, Formula IV) in the chromophore which will results in limited UV light absorption.

The third limitation of this quaternized water-soluble UV absorber meant for personal care application is that it does not impart any sensory effect on skin or conditioning effect on hair which is a much desired property of a cosmetic ingredient. The quaternized UV absorber like p-methoxy cinnamidopropyl dimethyl behenyl ammonium chloride (Formula VI, GalHueShield, CAS No 880645-41-0) has excellent sensory and conditioning properties however, it is water-insoluble and hence unsuitable for water-based clear formulations.

In view of these limitations of hitherto reported both water-soluble quaternary (Formula IV) and water-insoluble 'quaternized' UV absorbers (Formula V and VI) for water-based formulation for hair and skin, there is still a need in the art for the provision of a UV protector that would be a) water-soluble but highly substantive without being tacky, b) the quaternized UV absorber can be a protector for skin or hair care; c) shall offer ease of formulating in all sorts of formulation types e.g. creams, lotions, shampoos, conditioners, sprays, mousse etc., without restricting the usage level on account of destabilizing formulations.

In the present invention, all the three limitations, namely, 1) higher degree of substantivity to skin and hair surface, 2) UV absorption power and 3) the sensory and the conditioning effect, of current commercially available products have been efficiently addressed by providing novel and substantive water soluble quaternized UV absorbers and its use in personal care compositions.

Objectives of the Invention

Therefore, the objective of the present invention is to overcome the limitation of water-soluble quaternized UV

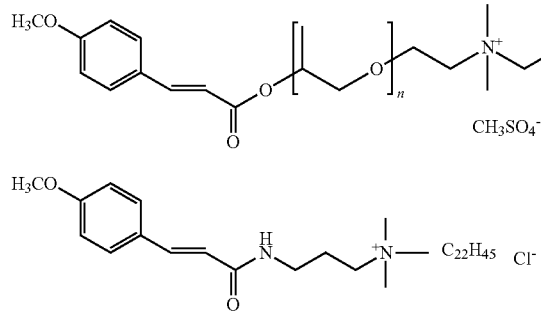

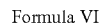

It is pertinent to mention here that water-soluble UV absorbers are needed for protecting artificially colored hair that would be substantive to hair and for protecting skin from solar radiation without imparting any tacky feel when applied via water-based (solvent-free) formulations like sprays or gels.

The commercially available quaternized water-soluble UV absorber (Formula IV) has limitation of being substantive in a very limited way since it has only one quaternary ammonium center thereby having limited affinity to skin surface per unit of light absorbing chromophore.

absorbers reported in the prior art in terms of substantivity to hair and skin surface. Another objective of the present invention is to create an easy-to-formulate water-soluble quaternized UV absorber that would impart conditioning/sensory effects while photo-protecting hair/skin and dyed hair from sunrays.

SUMMARY OF THE INVENTION

In line with the above objective, the present invention provides highly substantive quaternized water-soluble UV-absorbing compounds of Formula I wherein;

Formula I

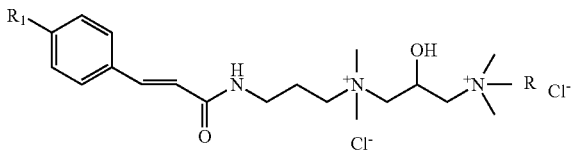

R is selected from saturated or unsaturated alkyl groups with $C_{12}$ to $C_{22}$ carbon atoms; $R^1$ is selected from either H or methoxy group.

In another aspect, the invention provides a process for preparation of UV absorbing compounds of formula I, which process comprises; reacting cinnamidopropyl dimethyl amine of Formula II with 2-hydroxyl 3-chloro propyl alkyl dimonium chloride of Formula III in aqueous medium to give the corresponding compound of Formula I.

Formula II

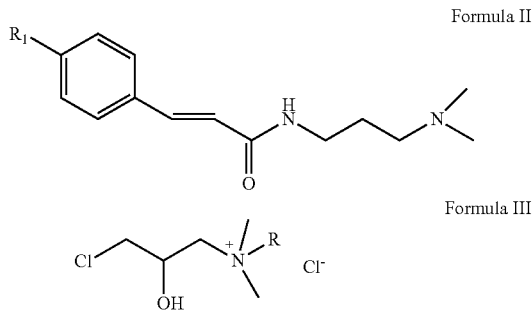

Formula III

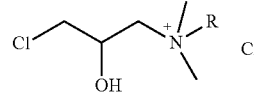

Wherein, R is selected from saturated or unsaturated alkyl groups with $C_{12}$ to $C_{22}$ carbon atoms; R1 is selected from either H or methoxy group.

In another aspect, the invention provides personal care compositions containing compounds of Formula I, as UV absorbers along with one or more ingredients selected from UV absorbers, quaternary conditioners, polymeric quaternary conditioners, silicones, natural polymers, film forming agents, moisturizers, vitamins, antidandruff agents, vegetable oils, petrolatum, humectants, protein derivatives, botanicals, emulsifying agents, surfactants, vitamins and rheology modifiers.

The doubly quaternized, water-soluble, UV-absorbing compound of Formula I according to the present invention is present in personal care compositions in an amount ranging from 0.1 to 15% by weight of the total composition.

The personal care compositions according to the invention may be selected from the group consisting of hair conditioners, shampoos, hair sprays, Aerosol Hair Mousse, Instant Hair-spray Conditioner, Hair styling gel, Sunscreen cream and lotions etc.

DETAILED DESCRIPTION OF THE INVENTION

Figure 1:
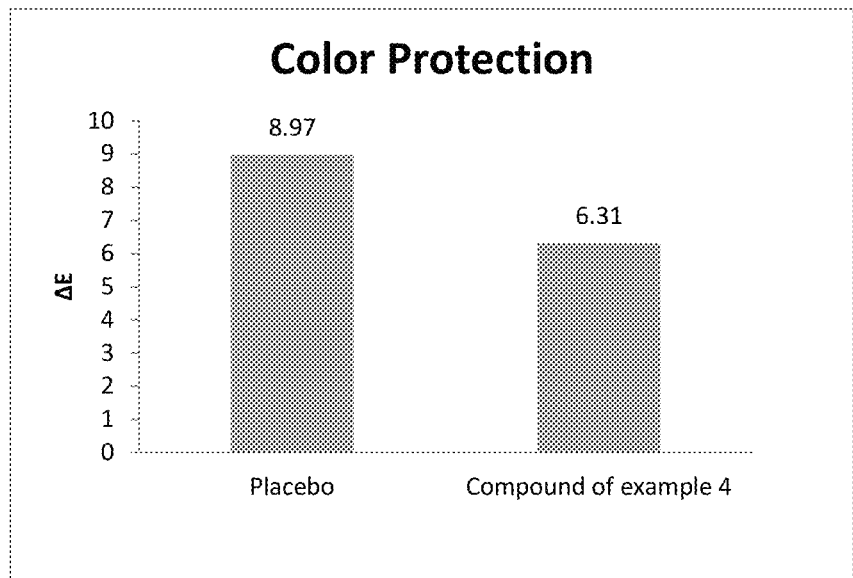
FIG. 1 depicts hair color protective effect of compounds of formula I (Anti-fade effect) from solar radiation

The invention will now be described in detail in connection with certain preferred and optional embodiments, so that various aspects thereof may be fully understood and appreciated.

As discussed above, there have been continuous attempts to create quaternized UV absorbers for hair care application, however, striking an optimal balance with respect to the three desired attributes, namely, a) high substantivity resulting in high UV protection b) good conditioning and sensory effects on hair and skin c) ease of incorporation or formulability, are difficult to achieve. In summary, the water-soluble quaternized UV absorbers that are currently available in the art suffer from the disadvantage of limited substantivity and no conditioning/lubricating effect on hair or skin (Incroquat UV 283). The substantive quaternized UV absorbers that are available in the market suffer from the disadvantage of being water-insoluble as well as oil-insoluble and hence difficult to formulate (for example, Gal-HueShield and ChromAveil).

Thus, in view of these serious limitations of the quaternized UV absorbers that are available today, there is a definite need to create a UV absorbing molecule that would be more substantive to keratinous surfaces, that would be water-soluble and would impart conditioning effect to the surface in addition to providing protection form the UV light.

Accordingly, the present invention discloses doubly quaternized UV absorbers of Formula I with cinnamido moiety with high UV absorption, with high substantivity and ease of formulability, Formula I

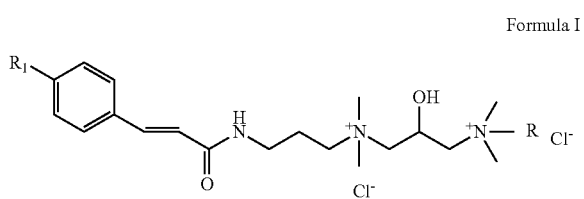

Wherein, R is selected from saturated or unsaturated alkyl groups with $C_{12}$ to $C_{22}$ carbon atoms; $R^1$ is selected from either H or methoxy group.

Representative compounds of Formula I according to the invention encompass the following compounds;
a) p-methoxy cinnamidopropyl (2-hydroxypropyl trimethyl ammonium chloride) dimonium chloride;
b) p-methoxy cinnamidopropyl (2-hydroxypropyl lauryl dimethyl ammonium chloride) dimonium chloride;
c) p-methoxy cinnamidopropyl (2-hydroxypropyl stearyl dimethyl ammonium chloride) dimonium chloride;
d) p-methoxy cinnamidopropyl 2, 3-dihydroxy propyl dimonium chloride.

In another embodiment, the invention provides process for preparation of UV absorbers of Formula I by quaternizing cinnamidopropyl dimethyl amines (Formula II) with quaternary ammonium agents (Formula III) in aqueous medium to obtain compounds of formula I in quantitative yields.

The process of the present invention is depicted in scheme 1.

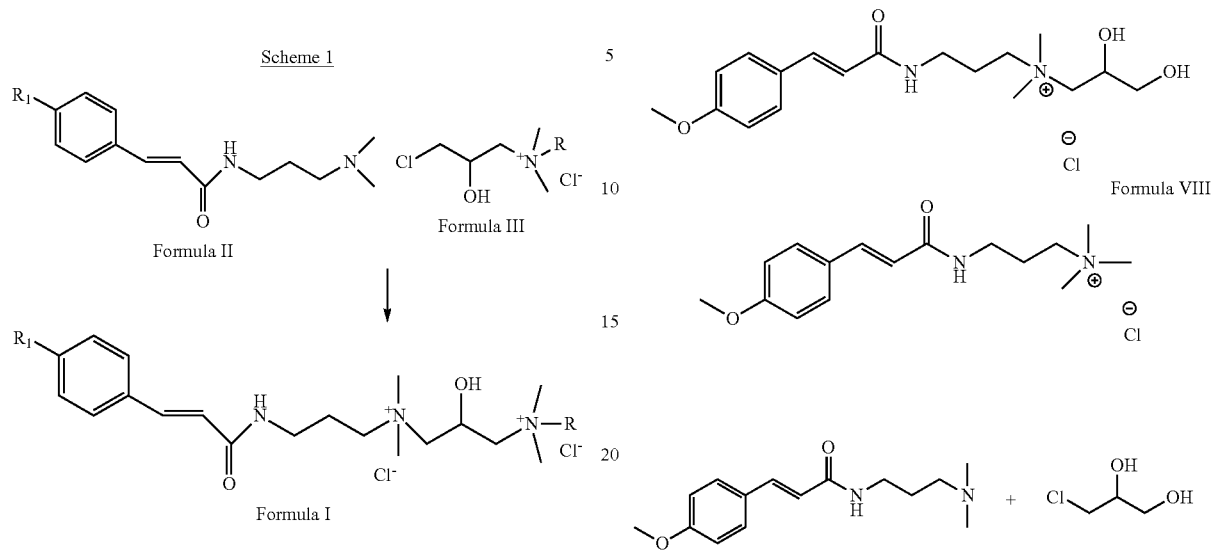

The UV absorbing chromophore p-methoxy cinnamido propyl dimethyl amine (Formula II, Scheme 1) is synthesized as per the method described in the literature (U.S. Pat. No. 9,463,337) by reacting p-methoxy cinnamoyl chloride with N, N dimethyl propyl diamine in aqueous Schotten Baumann type conditions (Example 1). This UV absorbing tertiary amine is then quaternized by 3-chloro 2-hydroxy propyl dimethyl alkyl ammonium chlorides (Formula III) that are commercially available by SKW QUAB Chemicals, USA (www.quab.com). Examples 2, 3 and 4 describe quaternization of Formula II with compounds of Formula III wherein R=$CH_3$, $C_{12}H_{25}$ and $C_{18}H_{37}$ to get the corresponding doubly quaternized UV absorbers of Formula I. (Scheme 1).

The quaternizing agents are available commercially by trade names of QUAB 188, QUAB 342, QUAB 426. The quaternization reactions are performed in water with equimolar stoichiometry by heating the stirred reaction mixture for 6 h at 85° C. Typically, the progress of reaction is monitored by estimation of chloride ion content of the reaction mass. The quaternization reaction is very facile and the yields are quantitative. Other QUABs are expected to exhibit same facility with quaternization of such tertiary sunscreen amines. The doubly quaternized products of Formula I, p-methoxy cinnamidopropyl (2-hydroxypropyl alkyl dimethyl ammonium chloride) dimonium chlorides are obtained as pale yellow colored aqueous solution. The final analysis of doubly quaternized quats (Formula I) in aqueous solutions showed very negligible amount of free unreacted cinnamidopropyl dimethyl amine of formula II.

Substantivity to Hair Through a Rinse-Off Conditioner Formulation:

In this embodiment, the substantivity of compounds of Formula I to hair (deposition of UV absorber on hair) are compared against other commercially available UV absorbers. Accordingly, singly quaternized UV absorbers (Formula VII and Formula VIII) are prepared in an analogous way as shown in Scheme 2 wherein p-methoxy cinnamidopropyl dimethyl amine is reacted with glyceryl α-monochlorohydrin and methyl chloride respectively (Example 5 and 6).

Further, the commercial water-soluble quaternized UV absorber, Incroquat UV 283 (Formula IV) and zwitterionic water-soluble UV absorber Galaxy SunBeat (Formula X) are procured from market.

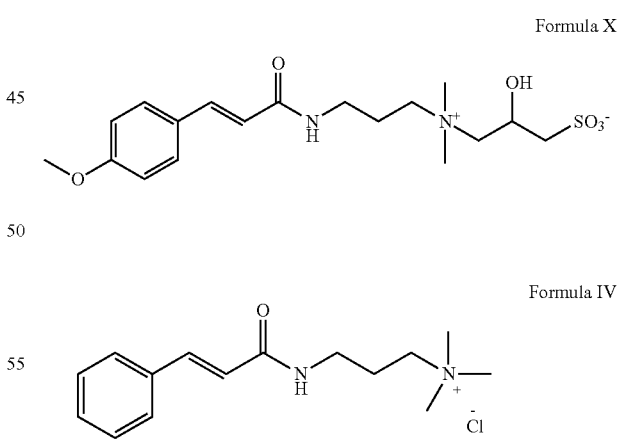

Accordingly, a representative compound of Formula I, p-methoxy cinnamidopropyl (2-hydroxypropyl stearyl dimethyl ammonium chloride) dimonium chloride (Formula IX), has been taken for comparison purpose with other singly quaternized UV absorbers (Cinnamido propyl trimethyl ammonium chloride, Incroquat UV 283 (Formula IV), p-methoxy cinnamidopropyl trimethyl ammonium chloride (Formula VII), p-methoxy cinnamidopropyl 2,3-dihydroxy propyl dimonium chloride (Formula VIII) for the substantivity on hair through a conditioner formulation and for demonstrating the ease of formulation and its superior surface activity. The synthesis of, p-methoxy cinnamidopropyl (2-hydroxypropyl stearyl dimethyl ammonium chloride) dimonium chloride (Formula IX), is described in Example No 4. The synthesis of p-methoxy cinnamidopropyl (2-hydroxypropyl trimethyl ammonium chloride) dimonium chloride, is described in Example 2.

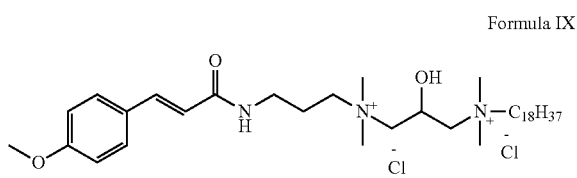

Formula IX

Rinse-off conditioner formulations prepared using quaternized UV absorbers and their relative substantivity is listed in Table II.

TABLE II

| Water-soluble UV absorber | Quaternary ammonium centers and | Relative Substantivity Mg/1.5 g of hair |
|---|---|---|
| Cinnamido propyl trimethyl ammonium chloride, Incroquat UV 283 (Formula IV) | One | 0.6 |
| p-methoxy cinnamidopropyl trimethyl ammonium chloride (Formula VII) | One | 0.65 |
| p-methoxy cinnamidopropyl 2,3-dihydroxy propyl dimonium chloride, Example 5 (Formula VIII) | One | 0.44 |
| 3-(N-p-methoxy cinnamidopropyl-N,N-dimethylammonium)-2-hydroxypropane-1-sulphonate (Galaxy SunBeat) zwitterionic, electrically neutral, Formula X) | One | 0.75 |
| p-methoxy cinnamidopropyl (2-hydroxypropyl stearyl dimethyl ammonium chloride) dimonium chloride Example 4 (Formula IX) | Two | 1.50 |
| p-methoxy cinnamidopropyl (2-hydroxypropyl trimethyl ammonium chloride) dimonium chloride, Example 2 | Two | 1.65 |

Relative substantivity through a rinse-off conditioner formulation and the applicatory protocol are described in Example 7. Rinse-off conditioner formulations are prepared using equimolar quantities of quaternized UV absorbers listed in Table II. The deposited quaternized UV absorber is re-extracted and measured conveniently using its UV absorbing property.

Interestingly, all four water-soluble UV absorbers of Table II with single quaternary center show significantly low deposition compared to the last two molecules of Formula I with two quaternary centers. p-methoxy cinnamidopropyl (2-hydroxypropyl stearyl dimethyl ammonium chloride) dimonium chloride, the compound of Formula I, (prepared as per Example 4), and p-methoxy cinnamidopropyl (2-hydroxypropyl trimethyl ammonium chloride) dimonium chloride, the compound of Formula I, (prepared as per Example 2), of the present invention are almost double or more than double thereby establishing higher substantivity when compared to other singly quaternized UV absorbers (Table II).

Hair Color Protection (Anti-Fade Effect) from Solar Radiation

In this embodiment, hair color protective effect of the compounds of Formula I are tested in hair tresses. Accordingly, the conditioner formulations (placebo and with compound of Example 4) are prepared as described by the formulation in the Example 7. The bleached hair tresses are shampooed by the placebo shampoo containing only sodium lauryl ether sulphate and cocoamidopropyl betaine and dyed using L'Oreal's Excellence HiColor H11 Intense Red hair color as per the protocol described by the dye manufacturer.

Hair coloring (hair dyeing) process is performed as recommended by the marketed product. The color and the developer are mixed in ratio of 1:1 and shampooed hair tresses are treated with the same. The color and developer mixture is applied uniformly to the hair tresses and covered with the aluminum foil for twenty minutes. After developing color, the hair tresses are washed with warm water. The colored hair tresses are divided into two groups, namely, placebo (colored hair treated with placebo shampoo and placebo rinse-off conditioner and exposed to UV light) and treated (colored hair treated with placebo shampoo and conditioner with UV absorber of Example 4 and exposed to UV light). The washing cycles comprise of shampooing, conditioning, rinsing and UV exposure as described in Example 8. The loss of color of the hair tresses 'Placebo' and 'Treated' is measured on the Hunter instrument, Labscan XE spectrophotometer. The total color loss ($\Delta E$) is assessed by the change in L* a* b* scale using the equation $\Delta E = [(\Delta L)^2 + (\Delta a)^2 + (\Delta b)^2]^{1/2}$. (FIG. 1)

Lower $\Delta E$ in case of the 'treated' set as compared to the 'placebo' set when compared with the 'control' showed that the significant anti-fade activity of the rinse-off conditioner with p-methoxy cinnamidopropyl (2-hydroxypropyl stearyl dimonium chloride) dimonium chloride of example 4.

Conditioning Effect and Reduction in Combing Force:

The conditioning effect is evaluated through conditioner formulation containing compound of Formula I (Example 4) as per the protocol described in the Example 9 (shampooing-conditioning) and measuring the % reduction in combing work using Dia-Stron tensile tester (MTT 175). It can be seen that with longer alkyl chain the combing ease increases and with double quaternary centers exhibits better conditioning and sensory properties (FIG. 2) on hair compared to another water-soluble quaternized UV absorbers with one quaternary center such as p-methoxy cinnamido propyl trimethyl ammonium chloride (Example 6) or p-methoxy cinnamidopropyl 2,3-dihydroxy propyl dimonium chloride (Example 5).

Surface-Active Properties

These doubly quaternized UV absorbers (Formula I, with R=long alkyl chain, $C_8H_{17}$ to $C_{22}H_{45}$) of the present invention exhibit good surface-active properties. They reduce the surface tension of water from 72 Mn/m to 35 Mn/m at 1.0% concentration, at 30° C. These quaternized UV absorbers behave like cationic surface active agents and can be easily titrated against an anionic surfactant as a standard for two-phase titration for the determination of active matter.

Silicones are used in hair care formulations for imparting silky smooth feel and shine (gloss). Often times they are converted into easy-to-formulate form by creating emulsions using anionic surfactant. Typical hair conditioners are cationic molecules (good affinity for negatively charged hair and skin surface) and the presence of anionic surfactant in silicone emulsions results in compatibility issue. However, the cationic UV light absorbing emulsifiers of the present invention can be used as silicone emulsifiers.

The compounds of Formula I of the present invention behave like cationic surfactant and their surface activity has been exploited in making extremely stable emulsion of dimethicone in water. The recipe described below in example 10 uses p-methoxycinnamidopropyl (2-hydroxypropyl stearyl, dimethyl ammonium chloride) dimonium chloride of Example 4 to create a stable emulsion. It can be seen from this example that almost 50% w/w dimethicone has been emulsified with quaternary ammonium surfactant of Example 4. It is also important to note here that the other singly cationic water-soluble or singly cationic water-dispersible UV absorbers do not yield a stable emulsion with dimethyl silicones.

Zeta potential of 1% dispersion of doubly quaternized UV absorber, Formula I, $R=C_{18}H_{37}$ and $R_1=OCH_3$ is found to be +47 mV (Zetasizer Nano, Malvern). This shows the presence of strong surface charge and hence the reason to be highly substantive to hair and skin surface. Also the high zeta potential (+46 mV) ensures the stability of colloidal formulations.

Antimicrobial Properties of Doubly Quaternized UV Absorbers

The doubly quaternized UV absorbers of Formula I ($R=C_8H_{17}$ to $C_{22}H_{45}$) according to the invention show decent antimicrobial properties. The minimum growth inhibitory concentrations against G +ve, G −ve bacteria and against the yeast for two compounds of Formula I of Example 3 and Example 4 are given in the Table III. This antimicrobial property is useful for preservation of personal care formulations. The antimicrobial activity against dandruff causing microorganism, *Malassezia furfur* is useful for hair care applications.

TABLE III

| Microorganism | Example 3; Formula I, R = $C_{12}H_{25}$, $R_1$ = $OCH_3$ | Example 4; Formula I, R = $C_{18}H_{37}$, $R_1$ = $OCH_3$ |
|---|---|---|
| *Staphylococcus aureus* ATCC6538 | 0.3% | 0.2% |
| *Escherichia coli* ATCC 10142 | 0.4% | 0.3% |
| *Pseudomonas aeruginosa* Immune type IV | 0.4% | 0.4% |
| *Propionibacterium acnes* MTCC 1951 | 0.5% | 0.4% |
| *Malassezia furfur* MTCC 1374 | 0.5% | 0.6% |
| *Candida albicans* ATCC 10231 | 0.3% | 0.3% |

Molecular Weights and Skin Penetration:

The doubly quaternized UV absorbers of the present invention (Formula I, $R=C_8H_{17}$ to $C_{22}H_{45}$) have molecular weight above 500 Dalton (580 to 744 g/m, Example 2, 3, 4) and thus are unlikely to penetrate the stratum corneum of the skin. And hence they can be considered dermatologically safe. (*The* 500 *Dalton rule for the skin penetration of chemical compounds and drugs*, Bos J. D, Meinardi M. M, Exp. Dermatol. 2000 June; 9(3):165-9)

The advantages of compounds of Formula I of the present invention ($R=C_{12}$ to $C_{22}$, $R_1=H$ or methoxy) are as follows:

1) These compounds of Formula I ($R=C_{12}$ to $C_{22}$, $R_1=H$ or methoxy) has superior protective effect of hair and skin from UV radiation of sunrays by absorbing the same than the currently available water-soluble UV absorbers.

2) The compounds of Formula I are more effective than the currently available water-soluble UV absorbers by virtue of being more substantive to hair and skin surfaces. The presence of two quaternary ammonium centers make these compounds of Formula I ($R=C_{12}$ to $C_{22}$, $R_1=H$ or methoxy) highly substantive to keratinous surfaces.

3) They exhibit good conditioning effect due to the presence of long alkyl chain as a part of the molecular structure. These compounds of the present invention align the damaged cuticles of hair surface and thereby enhance the sensorial attribute of the formulation.

4) The compounds of the present invention of Formula I, ($R=C_{12}$ to $C_{22}$, $R_1=H$ or methoxy), protect applied color (Anti-Fade) through regular hair care formulations like hair conditioners.

5) Molecular weights of the compounds of Formula I of the present invention ($R=C_{12}$, $R_1$=methoxy, Example 3, MW=604 and $R=C_{18}$, $R_1$=methoxy, Example 4, MW=688) are more than 500 Dalton and are significantly less likely to penetrate through the stratum corneum compared to water-soluble UV absorbers that are commercially available and thus safe for use in personal care formulations.

6) Compounds of Formula I ($R=C_{12}$ to $C_{22}$, $R_1=H$ or methoxy) exhibit good surface activity since they have all the necessary features to be cationic surfactants, the hydrophilic portion and hydrophobic portion. Reduction in the surface tension of water by 30 to 35 dynes demonstrated significant surface activity that can be exploited for forming cationic emulsions. Their unique structure resembles 'gemini' surfactants and significant lowering of surface tension supports this statement. The extraordinary utility as cationic emulsifier is demonstrated creating a very stable emulsion of dimethione (Example 9).

7) The compounds of Formula I of the present invention exhibit high water solubility (30 to 50%) and hence the extreme ease of incorporation in to personal care formulations particularly in single phase water-based formulations compared to known UV absorbers.

8) The compounds of Formula I ($R=C_{12}$ to $C_{22}$, $R_1=H$ or methoxy) of the present invention with their two quaternary ammonium centers exhibit surfactant like properties as well as good anti-bacterial properties. This is a very useful property for preservation of personal care formulation as well as to maintain good hygiene of skin and hair.

EXPERIMENTAL

The invention will now be illustrated with the help of examples.

Examples 1 to 4 describe the process of manufacture of the compounds of Formula I, p-methoxy cinnamidopropyl (2-hydroxypropyl alkyl, dimethyl ammonium chloride) dimonium chloride. Example 5 describes synthesis of p-methoxy cinnamidopropyl 2, 3-dihydroxy propyl dimonium chloride which is a cationic compound with same UV absorbing chromophore and one quaternary ammonium center. Example 6 describes synthesis of p-methoxy cinnamidopropyl trimethyl ammonium chloride with one quaternary ammonium center. Example 7 compares the relative substantivity (actual deposition on hair) to hair tresses of water-soluble UV absorbers with one quaternary center with water-soluble UV absorbers containing two quaternary centers. This comparative study is done via a rinse-off conditioner formulation. Experiment 8 showcases the effectiveness of one of the representative compounds of Formula I against the fading of the color due to solar radiation and due to washing. Experiment 9 demonstrates the excellent surfactant properties of compounds of Formula I that are employed in creating a stable translucent emulsion of dimethicone in water. Examples 7 to 17 illustrate the performance and the benefits of compounds of Formula I through the formulations.

Examples from 10 to 17 demonstrate a variety of hair care and skin care formulations where compound of Formula 1 with R=stearyl group is used as UV absorber.

These examples are by way of illustrations only and do not restrict the scope of the present invention. Many changes and modifications can be made within the scope of the present invention without departing from the spirit thereof and the invention concluded all such modifications.

Example 1

Synthesis of p-methoxycinnamido propyldimethylamine

To a stirred solution of N,N-dimethyl aminopropylamine (55.7 g 0.55 gmol) in water (35 mL) at room temperature, under nitrogen blanket, molten p-methoxy cinnamoyl chloride (103 g, 0.52 gmol) was slowly added while maintaining the temperature between 50 to 55° C. over the period of 1 h. The stirring was continued for additional two hours. At this stage, water (20 mL) was added and the reaction mixture was cooled to 10° C. and acidified with concentrated hydrochloric acid to pH of 2. The hydrochloride salt solution was filtered and the filtrate was basified using sodium hydroxide (45% solution) to the pH of 11. The precipitated p-methoxy cinnamidopropyl dimethyl amine was filtered, washed with water and dried under vacuum at 40° C. to yield the p-methoxycinnamido propyldimethylamine (amidoamine) (121.0 g, 89%) as pale yellow colored solid (mp 92° C.).

Molar extinction coefficient, $\in$, in methanol is 24,224 at 290 nm.

IR in dichloromethane shows carbonyl stretching of amide at 1660 $cm^{-1}$ and NH stretching at 3300 $cm^{-1}$.

$^1$H NMR (300 MHz, $CDCl_3$): δ 1.73 (p, 2H, J=6.6 Hz), 2.2 (s, 6H), 2.42 (t, 2H, J=6.6 Hz), 3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J=8.7 Hz), 7.53 (d, 1H, J=15.6 Hz).

$^{13}$C NMR (300 MHz, $CDCl_3$): δ 26.46, 39.18.45.43, 55.3058.29, 114.13, 118.99, 127.67, 129.24, 139.78, 160.63, 166.43.

Example 2

Synthesis of p-methoxy cinnamidopropyl (2-hydroxypropyl trimethyl ammonium chloride) dimonium chloride: Reaction of p-methoxy cinnamido propyl dimethyl amine and 3-chloro-2-hydroxy propyl trimethyl ammonium chloride A mixture of p-methoxy cinnamido propyl dimethyl amine (25 g, 0.095 gmol), 3-chloro-2-hydroxypropyl trimethyl ammonium chloride (27 g, 0.095 gmol, commercially available as 65% solution) and water (33 mL) under nitrogen was stirred at 85° C. for 6 hours. The progress of the reaction was monitored by the increase in the chloride ion content. The reaction was stopped when the amidoamine content is brought to less than 1.0%.

The quaternized product, p-methoxy cinnamidopropyl (2-hydroxypropyl trimethyl ammonium chloride) dimonium chloride was obtained as pale yellow colored aqueous solution with the following analysis.

Appearance: Pale yellow colored clear liquid, pH of 5% solution: 6.8, solids content=51%, free amidoamine content=0.45%, chloride ion content=7.8%

Molar extinction coefficient, $\in$, in water: 22,000 $mol^{-1}cm^{-1}$ at 290 nm. FTIR: 1655 $cm^{-1}$ (CO of amide), 3228, 3372 $cm^{-1}$ (broad stretch, OH, NH)

$^1$H NMR (300 MHz, $D_2O$): δ 2.02 to 2.1 (m, 2H), 3.16 to 3.58 (m, multiplet overlapping singlet of methyl groups on nitrogen, 24H), 6.36 (d, 1H, J=15.6 Hz), 6.9 (d, 2H, J=9 Hz), 7.35 (d, 1H, J=15.6 Hz), 7.46 (d, 2H, J=9 Hz).

Example 3

Synthesis of p-methoxy cinnamidopropyl (2-hydroxypropyl lauryl dimethyl ammonium chloride) dimonium chloride: Reaction of p-methoxy cinnamido propyl dimethyl amine and 3-chloro-2-hydroxy propyl lauryl dimethyl ammonium chloride A mixture of p-methoxy cinnamido propyl dimethyl amine (25 g, 0.095 gmol), 3-chloro-2-hydroxypropyl lauryl dimethyl ammonium chloride (81 g, 0.095 gmol, commercially available as 40% solution) and water (8.7 mL) under nitrogen was stirred at 85° C. for 6 hours. The progress of the reaction was monitored by the increase in the chloride ion content. The reaction was stopped when the amidoamine content is brought to less than 1.0%. The quaternized product, p-methoxy cinnamidopropyl (2-hydroxypropyl lauryl dimethyl ammonium chloride) dimonium chloride was obtained as pale yellow colored aqueous solution with the following analysis Appearance: Pale yellow colored clear liquid, pH of 5% solution: 6.8, solids content=51%, free amidoamine content=0.5%, chloride ion content=5.9%

Molar extinction coefficient, $\in$, in water: 19,500 $mol^{-1}cm^{-1}$ at 305 nm. FTIR: 1655 $cm^{-1}$ (CO of amide), 2854, 2904 $cm^{-1}$ (CH), 3228, 3372 $cm^{-1}$ (broad stretch, OH, NH)

$^1$H NMR (300 MHz, $D_2O$): δ 0.85 to 0.89 (m, 3H), 1.05 to 1.15 (m, 22H) 3.0 to 3.17 to 3.76 (m, 23H), 3.8 (s, 3H), 6.56 (d, 1H, J=15 Hz), 6.8 (d, 2H, J=9 Hz), 7.38 (d, 1H, J=15 Hz), 7.45 (d, 2H, J=9 Hz)

Example 4

Synthesis of p-methoxy cinnamidopropyl (2-hydroxypropyl stearyl dimethyl ammonium chloride) dimonium chloride: Reaction of p-methoxy cinnamido propyl dimethyl amine and 3-chloro-2-hydroxy propyl stearyl dimethyl ammonium chloride A mixture of p-methoxy cinnamido propyl dimethyl amine (13.8 g, 0.05 gmol), 3-chloro-2-hydroxypropyl stearyl dimethyl ammonium chloride (53.25 g, 0.05 gmol, commercially available as 40% solution in water and propylene glycol in 1:1 ratio) and water (46 mL) under nitrogen was stirred at 85° C. for 6 hours. The progress of the reaction was monitored by the increase in the chloride ion content. The reaction was stopped when the amido amine content is brought to less than 1.0%. The quaternized product, p-methoxy cinnamidopropyl (2-hydroxypropyl stearyl dimethyl ammonium chloride) dimonium chloride is obtained as pale yellow colored aqueous solution with the following analysis.

Appearance: Pale yellow colored clear liquid, pH of 5% solution 6.9, solids content=30.2%, free amidoamine content=0.4%, chloride ion content=3.1%

Molar extinction coefficient, ∈, in water: 19,700 mol$^{-1}$cm$^{-1}$ at 307 nm. Zeta potential: +46 mV, Charge density: 0.3066 meq/gram Surface activity: Surface effectiveness is 34.2 mN/m whereas surface efficiency (–log C20) was found to be 6.23. Critical micelle concentration at 25° C. is 2.29×10$^{-3}$ mM FTIR: 1662 cm$^{-1}$ (CO of amide), 2852, 2922 cm$^{-1}$ (CH), 3250, cm$^{-1}$ (broad stretch, OH)

$^1$H NMR (300 MHz, D$_2$O): δ 0.85 to 0.89 (m, 3H), 1.05 to 1.15 (m, 34H) 3.0 to 3.17 to 3.76 (m, 23H), 3.8 (s, 3H), 6.56 (d, 1H, J=15 Hz), 6.8 (d, 2H, J=9 Hz), 7.38 (d, 1H, J=15 Hz), 7.45 (d, 2H, J=9 Hz)

$^{13}$C NMR (300 MHz, D$_2$O): 14.16, 22.71, 22.87, 26.37, 29.39, 29.69, 29.77, 31.94, 51.77, 52, 86, 53.31, 61.62 66.77, 114.24, 129.60, 160.79

Example 5

Synthesis of p-methoxy cinnamidopropyl 2, 3-dihydroxy propyl dimonium chloride: Reaction of p-methoxy cinnamido propyl dimethyl amine and glyceryl α-monochlorohydrin A mixture of p-methoxy cinnamido propyl dimethyl amine (39.3 g, 0.15 gmol), glyceryl α-monochloro hydrin (16.6 g, 0.15 gmol) and water (129 mL) under nitrogen was stirred at 85° C. for 6 hours. The progress of the reaction was monitored by the increase in the chloride ion content. The reaction was stopped when the starting material cinnmidopropylamine content is brought to less than 0.5%. The quaternized product, p-methoxy cinnamidopropyl 2, 3-dihydroxy propyl dimonium chloride was obtained as clear pale yellow colored aqueous solution (186 g) with the following analysis.

pH of 5% solution: 7.1, solids content=30% and chloride ion=2.9%

Example 6

Synthesis of p-methoxy cinnamidopropyl trimethyl ammonium chloride: Reaction of p-methoxy cinnamido propyl dimethyl amine and methyl chloride A mixture of p-methoxy cinnamido propyl dimethyl amine (44 g (89.5%) (0.15 gmol), methyl chloride 8.4 g, (0.165 gmol) and methanol 110 mL) in a sealed reactor was stirred at 110° C. for 6 hours. The progress of the reaction was monitored by the increase in the chloride ion content as well as ceasation of drop in the pressure reading on the guage. The reaction was stopped when the starting material cinnmidopropylamine content is brought to less than 0.5%. The solvent was removed using a rotary evaporator and the residue was redissolved in water to get 30 aqueous solution. The quaternized product, p-methoxy cinnamidopropyl trimethyl ammonium chloride was obtained as clear pale yellow colored aqueous solution (155 g) with the following analysis.

pH of 5% solution: 4.15, solids content=30% and chloride ion=3.3%

Example 7

Comparison Between Quaternized UV Absorbers with One Quaternary Center (Incroquat UV 283 (Formula IV), Galaxy SunBeat (Formula 10), Example 5 and Example 6) Versus Double Quaternized UV Absorber (Example 4) for Substantivity to Hair Through Rinse-Off Conditioner Formulations Rinse-off conditioner formulations with quaternized UV absorbers of Example 4, 5, 6 and Incroquat UV 283 and Galaxy SunBeat are prepared as per the recipe given below.

Phase A and phase B of the table below are separately heated to about 75-80° C. in water-bath with stirring. After achieving the temperature, phase B was added to phase A with constant stirring. Then the formulation was immediately subjected to homogenization at high frequency. The process was continued until proper homogenization is achieved. The emulsion was then cooled with continued stirring. At 40° C., phase C was added. The contents are allowed to mix for about 10 min. and mixing was continued for additional 1 hour. Finally, pH was adjusted to 3.5 to 4.0 with 25% (w/w) citric acid solution.

Rinse-Off Conditioner Formulation

|  | Ingredients | Concentration (% w/w) |
|---|---|---|
| Phase A | Water | Balance to 100.0% |
|  | Hydroxyethyl Cellulose | 1.5 |
|  | Glycerin | 7.0 |
|  | EDTA disodium salt | 0.1 |
|  | Compound of Example 4 or 5 or 6 or Galaxy SunBeat or Incroquat UV283 | 0.0015 gmoles |
| Phase B | Mineral Oil | 6.0 |
|  | Cetyl Alcohol | 1.5 |
|  | Glyceryl monostearate | 3.5 |
| Phase C | Preservative | 0.5 |
|  | Citric acid | q.s. to adjust pH |
|  | Total | 100.0 |

Substantivity of Quaternized UV Absorber to Hair Via Rinse-Off Conditioner:

Hair tresses (1.5 g) were treated with shampoo (0.5 g) for 1 minute and rinsed under running tap water for 30 seconds. Rinse-off conditioner (0.5 g) was applied to the hair for 1 minute and rinsed under running tap water for 30 seconds. The deposited UV absorbers were then extracted by hot ethanol (reflux for 90 min) and the extracted amount is quantified by UV spectroscopy.

The UV spectroscopic analysis revealed that the deposition of compound of Example 4 (1.5 mg/1.5 g of hair) is found to be two times more substantive than p-methoxy cinnamidopropyl trimethyl ammonium chloride (Formula VII) compound of Example of 6 (0. 0.65 mg/1.5 g of hair) and Inqroquat UV 283 (Cinnamido propyl trimethyl ammonium chloride, (Formula IV, 0. 0.65 mg/1.5 g of hair) that have only one quaternary ammonium center for adhering to hair surface. p-Methoxy cinnamidopropyl (2-hydroxypropyl stearyl dimethyl ammonium chloride) dimonium chloride (compound of Example 4) and p-methoxy cinnamidopropyl (2-hydroxypropyl trimethyl ammonium chloride) dimonium chloride, (compound of Example 2, with two quaternary ammonium centers have been found to be at least two times more substantive when compared to other molecules listed in Table I with one quaternary center.

Example 8

Hair Color Protection Through a Rinse-Off Conditioner Formulation Containing Compound of Example 4

The photo-protection study was performed as per the protocol described in the literature by A. Howe et al., Color Care—Formulation Concepts, SOFW, 140, 1/2-2014. A typical placebo shampoo formulation was prepared (using sodium laureth sulphate 10% w/w, cocoamidopropyl betaine 4% w/w, salt 2.5% w/w, rest is water) and a conditioner formulation with the compound of Example 4 was prepared as per the formula given in Example 7. Bleached Indian hair tresses (180 mm long, 2.5 g) were washed with 20% SLES solution and air-dried, followed by bleaching with hydrogen peroxide. The hair tresses were then colored by L'Oreal Excellence HiColor H11 Intense Red hair color as per the guidelines prescribed on the color tube. After this, the hair tresses were washed with water and air-dried. The colored hair tresses were then subjected to seven applications on seven days, one application per day comprising shampooing, conditioning and exposing it to sunlight. Every application consisted of placebo shampoo application for 1 minute and rinsing off under running tap water for 30 seconds, followed by the conditioner application in the same manner. After every application, the hair tresses were dried and exposed to sunlight for 6 hours, thereby total exposure being 42 hours, followed by colorimetric measurements on L*, a*, b* scale using Chromameter CR400 (Konica Minolta). The color loss ($\Delta E$) between test sample and placebo was considered as the measure of color protection achieved after seven applications. The color protecting effect of compound of Example 4 against placebo is demonstrated in FIG. 1.

Example 9

Evaluation of % Combing Work Reduction

Bleached Indian hair tresses (180 mm long, 2.5 g) were treated with 10% SLES and dried. The combing resistance of these tresses was then measured in terms of the force required to pull a comb through them. Each tress was combed on the Dia-Stron tensile tester (MTT 175). Experimental conditions maintained are temperature of 25° C. and relative humidity of 55%.

Figure 2:
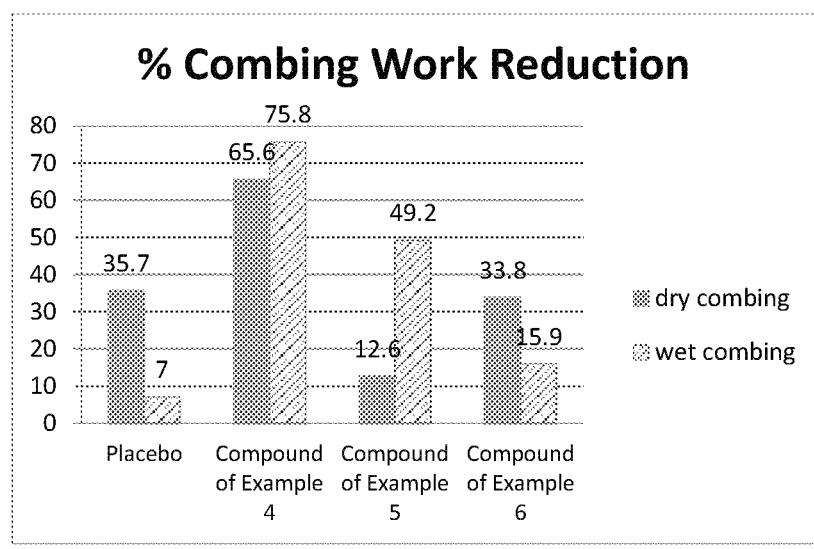
FIG. 2 depicts conditioning effect and reduction in combing force of compounds of formula I

Hard rubber comb was used for the analysis. Ten combing strokes were conducted for each tress and averaged to obtain a representative value. After the average combing force is determined for each wet tress, the tresses were allowed to dry at room temperature before average combing force is measured on the dry tresses. In the similar manner both wet and dry combing force was measured for the hair tress treated with a placebo shampoo (0.5 g) followed by treatment with conditioners (0.0015 gmole) based on compound of Example 4, compounds of Example 5 and Example 6 and a Placebo conditioner. The percent combing work reduction is depicted in FIG. 2.

Example 10

Emulsification of Dimethicone Using Doubly Quaternized UV Absorber of Example 4, p-Methoxy Cinnamidopropyl (2-hydroxypropyl Stearyl Dimethyl Ammonium Chloride) Dimonium Chloride To a stirred solution of Example 4 (41 g, 59.59 mmol) at room temperature, dimethicone (49.5 g, DC 200 from Dow Chemicals) was added slowly and stirring is continued for 10 min using Silverson homogenizer LSM. Water (9.5 mL) was added slowly and the mix was further homogenized at 5000 rpm for 30 min. The emulsion (100 g) thus obtained was observed to be stable at 5, 25 and 40° C. for 24 weeks.

Example 11

Color Protection Shampoo

| Phase A | |
|---|---|
| Deionized water | Balance to 100.0% |
| Compound of Formula I (Ex 4) | 4.0% |
| Phase B | |
| Sodium lauryl ether sulphate (28%) | 30% |
| Sodium lauroyl sarcosinate (30%) | 10% |
| Cocoamido propyl betaine (30%) | 5% |
| PEG 150 distearate | 0.5% |
| Ethylene Glycol distearate | 2.0% |
| Phase C | |
| Deionized water | 10% |
| Disodium EDTA | 0.1% |
| Galguard Trident (phenoxy ethanol, capryloyl glycine and undecylenoyl glycine) | 1.0% |
| Phase D | |
| Fragrance | 1.0% |
| Citric acid | q.s. to adjust pH |

Procedure:

All ingredients of Phase B were heated together to 75° C. with continuous stirring. To the stirred Phase B, Phase A was added and mixed till it becomes homogeneous. To this mixture, Phase C was added and stirring continued. The whole mass was cooled under stirring to room temperature and pH was adjusted with citric acid to 5.5 if necessary. This was followed by the addition of fragrance and color.

Example 12

'Sulphate-Free' Color Protection Shampoo

| Phase A | |
|---|---|
| Deionized water | Balance to 100.0% |
| Guar hydroxypropyl trimonnium chloride | 0.2% |
| Compound of Formula I (Ex 4) | 4.0% |
| Phase B | |
| Sodium cocoyl glycinate (30%) | 5% |
| Sodium lauroyl sarcosinate (30%) | 10% |
| Sodium cocoyl taurate (40%) | 15 |
| Alkyl poly glucoside (C8/C10) | 5% |
| PEG 150 distearate | 1.7% |
| Ethylene Glycol distearate | 2.0% |
| Phase C | |
| Deionized water | 10% |
| PEG 12 dimethicone | 0.5% |
| Disodium EDTA | 0.1% |
| Galguard Trident (Phenoxy ethanol, capryloyl glycine and undecylenoyl glycine) | 1.0% |
| Phase D | |
| Fragrance | 1.0% |
| Citric acid | q.s. to adjust pH |

Procedure:

Guar hydroxyl propyl trimonium chloride was dispersed in water by continuous agitation and to it Compound of Example 4 was added. All ingredients of Phase B were heated together to 75° C. under continuous stirring. To the stirred Phase B, Phase A was added and mixed till it becomes homogeneous. To this mixture, Phase C was added and stirring was continued. The whole mass was cooled under stirring to room temperature and pH was adjusted with citric acid to 5.5 if necessary. This was followed by the addition of fragrance and color.

Example 13

Color Protecting Hair Conditioner

| Phase A | |
|---|---|
| Deionized water | Balance to 100.0% |
| Glycerine | 10.0% |
| Hydroxy ethyl cellulose | 1.2% |
| Compound of Formula I (Ex 4) | 4.0% |
| PEG 7 Glyceryl cocoate | 2.0% |
| Disodium EDTA | 0.1% |
| Phase B | |
| Light Liquid paraffin | 8% |
| Cetostearyl alcohol | 5% |
| Cyclomethicone | 1.0% |
| Phase C | |
| Deionized water | 5% |
| Disodium EDTA | 0.1% |
| Galguard Trident (Phenoxy ethanol, capryloyl glycine and undecylenoyl glycine) | 1.0% |
| Phase D | |
| Fragrance | 1.0% |

Procedure:

All ingredients of Phase B were heated together to 75° C. with continuous stirring. To the stirred Phase B, Phase A was added and mixed till it becomes homogeneous. To this, Phase C was added and stirring continued. The whole mass was cooled under stirring to room temperature. This was followed by the addition of fragrance and color.

Example 14

Solvent-Free, Preservative-Free Color Protecting Hair Spray

| Deionized water | Balance to 100 |
|---|---|
| Compound of Formula I (Example 4) | 4.0% |
| PEG-12 dimethicone | 1.0% |
| Fragrance | 1.0% |
| Disodium EDTA | 0.1% |
| Sodium hydroxide | q.s. to adjust pH |

Procedure:

All ingredients were easily soluble in water. It was gently stirred to get the uniform solution that is transparent with pH ranging from 6.5 to 7.0. Challenge test as per CTFA protocol showed it to be meeting the prescribed criteria.

Example 15

Aqueous Color-Protecting Aerosol Hair Mousse

| Deionized water | Balance to 100.0% |
|---|---|
| Compound of Formula I (Example 4) | 4.0% |
| Cocoamido propyl betaine | 1% |
| Water-soluble silicone | 1.0% |
| Glycerin | 0.5 |
| Fragrance | 1.0% |
| Disodium EDTA | 0.1% |
| Propane/Isobutane propellant | 6.0% |

Procedure:

All ingredients were mixed together to get a uniform solution with viscosity of <100 cps. Challenge test as per CTFA protocol showed it to be meeting the prescribed passing criteria.

Example 16

Instant Hair-Spray Conditione

| Phase A | |
|---|---|
| Deionized water | Balance to 100.0% |
| Carbopol Aqua SF1 (Acrylate copolymer) | 5.0% |
| Phase B | |
| Deionized water | 40% |
| Compound of Formula I (Example 4) | 4.0% |
| Fragrance | 1.0% |
| Disodium EDTA | 0.1% |
| Phase C | |
| Sodium Hydroxide | q.s. to adjust pH |

Procedure:

Phase A and Phase B were prepared separately and mixed together under stirring. Sodium hydroxide was then added to

Example 17

Conditioner Formulation Using Emulsion of Example 10

| Phase A | |
| --- | --- |
| Distilled water | Balance to 100.0% |
| Hydroxyethyl Cellulose | 1.5% |
| Disodium EDTA | 0.1% |
| Glycerin | 7.0% |
| Phase B | |
| Light Liquid Paraffin | 6.0% |
| Glyceryl monostearate | 3.5% |
| Cetyl alcohol | 1.5% |
| Phase C | |
| Galguard Trident (phenoxy ethanol, capryloyl glycine and undecylenoyl glycine | 1.5% |
| Microemulsion of Example 10 | 10.0% |
| Phase D | |
| Citric acid | Q.S. to pH = 3.7 |

Procedure:

Phases A & B were heated separately to 70° C. with continuous stirring. To the Phase A, Phase B was added and homogenized at 5000 rpm using homogenizer (Silverson) for 15 minutes. The whole mass was cooled under stirring to room temperature and Phase C was added to it. pH of the formulation was adjusted with citric acid to 3.7

Example 18

Hair Styling Gel Using Cationic Polymers

| Polyquaternium 7 (9% active) | 30 g |
| --- | --- |
| Compound of Formula I (Ex 4) | 2.5 g |
| Water | 67.0 g |
| Benzoic acid | 0.5 g |
| pH (citric acid) | 5.5 |
| Viscosity | 6,500 |

Procedure:

Polyquaternium 7 with solids content of 9% and preserved with benzoic acid, having viscosity of 14,000 cps was slowly added to stirred water containing compound of Formula I and sodium benzoate. Adjusted the pH with citric acid if necessary to 5.5.

Example 19

Sunscreen Cream with SPF 15

| | % w/w |
| --- | --- |
| Phase A | |
| Water | 57.15 |
| Glycerine | 2 |
| Lauryl alcohol ethoxylate (9EO) | 0.5 |
| PEG-7-Glyceryl cocoate | 2 |
| EDTA disodium salt | 0.05 |
| Phase B | |
| Octocrylene | 3 |
| Avobenzone | 3 |
| Octyl methoxy cinnamate | 5 |
| Compound of Formula I (Ex 4) | 2.3 |
| Paraffin oil | 4 |
| Phenoxy ethanol | 1 |
| Stearic acid | 2 |
| Glyceryl mono stearate | 7 |
| Ceto stearyl alcohol | 6 |
| Isopropyl myristate | 5 |

Phases A & B were heated separately to 70° C. with continuous stirring. To the Phase A, Phase B was added and homogenized at 5000 rpm using homogenizer (Silverson) for 30 minutes. The whole mass was cooled under stirring to room temperature and pH of the formulation was adjusted with citric acid if it goes out the range of 5 to 7.

We claim:

1. Water-soluble UV absorbing compounds of Formula I with two quaternary ammonium centers, wherein;

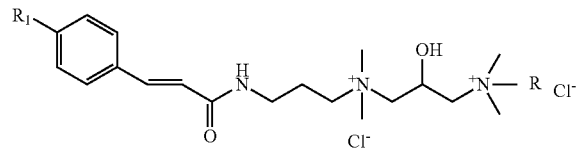

Formula I

R is selected from saturated or unsaturated alkyl groups with $C_{12}$ to $C_{22}$ carbon atoms and $R_1$ is selected from H or methoxy group.

2. The water-soluble UV absorbing compounds of claim 1, wherein the compound of is selected from the group consisting of:
   a) p-methoxy cinnamidopropyl (2-hydroxypropyl trimethyl ammonium chloride) dimonium chloride;
   b) p-methoxy cinnamidopropyl (2-hydroxypropyl lauryl dimethyl ammonium chloride) dimonium chloride;
   c) p-methoxy cinnamidopropyl (2-hydroxypropyl stearyl dimethyl ammonium chloride) dimonium chloride; and
   d) p-methoxy cinnamidopropyl 2, 3-dihydroxy propyl dimonium chloride.

3. A process for synthesis of water-soluble, quaternized UV absorbing compounds of Formula I

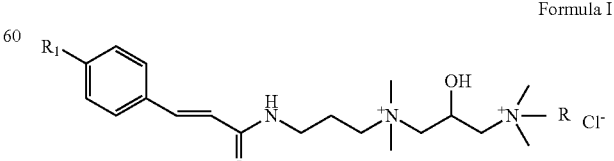

Formula I comprising: reacting cinnamidopropyl dimethyl amine of Formula II with 2-hydroxyl-3-chloro propyl alkyl dimonium chloride of Formula III in aqueous medium at 80 to 90° C.,

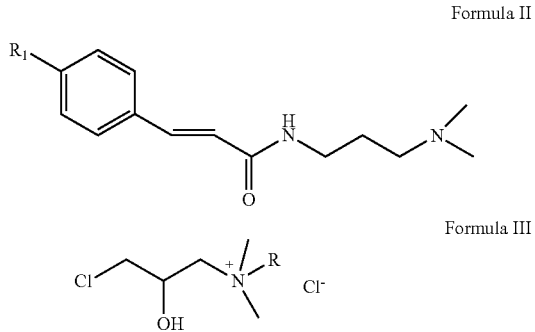

Formula II

Formula III wherein, R is selected from saturated or unsaturated alkyl groups with $C_{12}$ to $C_{22}$ carbon atoms and $R_1$ is selected from either H or methoxy group.

4. A personal care composition comprising doubly quaternized, water-soluble compounds of Formula I and one or more ingredients selected from UV absorbers, quaternary conditioners, polymeric quaternary conditioners, silicones, natural polymers, film forming agents, moisturizers, vitamins, antidandruff agents, vegetable oils, petrolatum, humectants, protein derivatives, botanicals, emulsifying agents, surfactants, vitamins and rheology modifiers.

5. The personal care composition as claimed in claim 4 wherein; the doubly quaternized, water-soluble, UV-absorbing compound of Formula I is present in an amount ranging from 0.1 to 15% by weight of the total composition.

6. The personal care compositions of claim 4, wherein the composition is selected from the group consisting of hair conditioners, shampoos, hair sprays, Aerosol Hair Mousse, Instant Hair-spray Conditioner, Hair styling gel, Sunscreen creams and lotions.

* * * * *